United States Patent [19]

Lafferty et al.

[11] 4,140,741
[45] Feb. 20, 1979

[54] USE OF CYCLIC CARBONIC ACID ESTERS AS SOLVENTS FOR POLY-(β-HYDROXYBUTYRIC ACID)

[75] Inventors: Robert M. Lafferty; Elmar Heinzle, both of Graz, Austria

[73] Assignee: Agroferm A.G., Chur, Switzerland

[21] Appl. No.: 868,795

[22] Filed: Jan. 12, 1978

Related U.S. Application Data

[62] Division of Ser. No. 758,647, Jan. 12, 1977, Pat. No. 4,101,533.

[30] Foreign Application Priority Data

Jan. 14, 1976 [CH] Switzerland .................. 403/76

[51] Int. Cl.$^2$ .................. C08G 63/06; C08G 63/72
[52] U.S. Cl. .................. 264/184; 195/2; 528/491
[58] Field of Search .................. 528/491; 264/184

[56] References Cited

U.S. PATENT DOCUMENTS

| | | | |
|---|---|---|---|
| 3,036,959 | 5/1962 | Baptist | 195/47 |
| 3,044,942 | 7/1962 | Baptist | 195/47 |
| 3,275,610 | 9/1966 | Coty | 260/80 |

FOREIGN PATENT DOCUMENTS 1201523  8/1970  United Kingdom.

OTHER PUBLICATIONS

Smith et al., "Metabolism of poly-(β-hydroxybutyrate)", Chemical Abstracts 69, 102949h (1968).

Primary Examiner—Lester L. Lee
Assistant Examiner—E. A. Nielsen
Attorney, Agent, or Firm—Merriam, Marshall & Bicknell

[57] ABSTRACT

The use of cyclic carbonic acid esters of the formula:

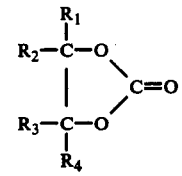

wherein $R_1$, $R_2$, $R_3$ and $R_4$, which may be the same or different, are hydrogen or alkyl with 1 to 6 C-atoms, as a solvent for racemic or optically active poly-(β-hydroxybutyric acid).

The preferred embodiment uses hot (120 to 150° C) ethylene carbonate or 1,2-propylene carbonate to extract poly-(β-hydroxybutyric acid) from moist or dry fermentation masses. These solvents have the advantage that the extracted poly-(β-hydroxybutyric acid) is precipitated in good yield from them on cooling. In addition they may be recycled without the need for a solvent regeneration step. These cyclic carbonic acid esters may also be used as the solvent in the processing of poly-(β-hydroxybutyric acid) by e.g. wet spinning.

6 Claims, No Drawings

USE OF CYCLIC CARBONIC ACID ESTERS AS SOLVENTS FOR POLY-(β-HYDROXYBUTYRIC ACID)

This is a division of application Ser. No. 758,647, filed Jan. 12, 1977, issued July 18, 1978 as U.S. Pat. No. 4,101,533.

The ability, widespread among microorganisms, to synthesise poly-(D-β-hydroxybutyric acid) as an energy store has been known for a long time (see e.g. the review by A. H. Rose and D. W. Tempest in Adv. Microbial Physiol. 10, 203–257, 1973). There has also been no lack of attempts to use this fermentation polyester (subsequently referred to as PHB) profitably (see U.S. Pat. No. 3,036,959 and U.S. Pat. No. 3,044,942).

The hitherto known methods of producing and recovering PHB have proved to be unpractical and uneconomic because extremely large amounts of solvents are consumed and complex and costly precipitation steps are necessary. In addition, the solvents can only be recycled in the known methods by using expensive, inefficient regeneration methods since the solvents either have too low boiling points to be separated by distillation or are miscible with water or the precipitants, forming azeotropic mixtures. For this reason the PHB containing fermentation mass has to be subjected to an expensive drying step before the extraction takes place. Furthermore, the hitherto used solvents and precipitants are damaging to health and their use involves a high explosion risk.

It has now been found that cyclic carbonic acid esters of the formula:

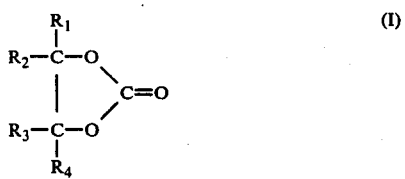

wherein $R_1$, $R_2$, $R_3$ and $R_4$, which may be the same or different, are hydrogen or alkyl with 1 to 6 C-atoms, preferably 1 to 4 C-atoms, in particular 1 or 2 C-atoms, are particularly suitable solvents for racemic and optically active poly-(β-hydroxybutyric acid). The compound of formula I, wherein $R_1$, $R_2$, $R_3$ and $R_4$ are hydrogen, i.e. ethylene carbonate, and the compound of formula I, wherein $R_1$, $R_2$ and $R_3$ are hydrogen and $R_4$ is methyl, i.e. 1,2-propylene carbonate, have been produced on a large scale since 1970 (G. Hechler, Chem. Ing. Technik 43, 903–905, 1971) and are used for instance in synthetic polymer chemistry.

It has been found that the problems outlined above can be solved or eliminated and the PHB obtained directly and very simply in pure form by using cyclic carbonic acid esters of formula I, in particular ethylene carbonate and/or 1,2-propylene carbonate, as solvents for the extraction of PHB from PHB containing fermentation masses, in particular the moist cell mass of PHB containing protophytes and protozoa.

Solutions of racemic or optically active poly-(β-hydroxybutyric acid) in cyclic carbonic acid esters of formula I, in particular ethylene carbonate and/or 1,2-propylene carbonate, are also suitable for the further processing of poly-(β-hydroxybutyric acid), e.g. wet spinning.

The invention thus relates to the use of cyclic carbonic acid esters of formula I, in particular ethylene carbonate and/or 1,2-propylene carbonate, as solvents for racemic or optically active poly-(β-hydroxybutyric acid), particularly for the extraction of PHB from fermentation masses or for the further processing of racemic or optically active poly-(β-hydroxybutyric acid), e.g. by wet spinning.

The extraction of PHB from fermentation masses can, depending on the solvent used and on the conditions employed, lead to a certain degree of depolymerisation, which in some circumstances may be undesirable since the properties of the extracted PHB are dependent on the molecular weight. Extraction with ethylene carbonate has been shown to result in a greater degree of depolymerisation than the use of 1,2-propylene carbonate.

The extraction of microbiologically produced PHB from the cell masses can be carried out as follows:

The cell mass is separated from the nutritive solution by decanting, filtering or centrifuging and suspended in a cyclic carbonic acid ester of formula I, in particular ethylene carbonate and/or 1,2-propylene carbonate. The suspension is then heated with stirring, it being possible to influence the rate of extraction and the molecular weight of the extracted PHB by the choice of temperature and the length of time the suspension is heated with stirring. The extracted cell mass is separated from the hot extract by decanting, filtering or centrifuging. Pure PHB is precipitated from the liquid thus obtained by cooling or by adding a little water and the precipitate separated off. The recovered solvent of formula I can be used repeatedly for further extractions of PHB from fermentation masses.

The following examples explain the invention.

The microorganisms and conditions employed in the production of PHB are described in the literature and will not therefore be described in detail. They are described in e.g. the review by Rose and Tempest (loc. cit.) and the article by H. G. Schlegel and G. Gottschalk (Angew. Chemie 74, 342–347, 1962).

The poly-(β-hydroxybutyric acid) was determined by the method of J. H. Law and R. A. Slepecky (J. Bact. 82, 33, 1961) or gravimetrically in the way described below.

(1) Precipitation from ethylenecarbonate: The hot solution of poly-(β-hydroxybutyric acid) in ethylene carbonate was cooled to 60° C. and diluted with an equal volume of water. The precipitate was separated by filtering through a weighed filter paper, washed with water and the filter with the precipitate dried overnight at 110° C. and then weighed.

(2) Precipitation from 1,2-propylene carbonate: The hot solution of poly-(β-hydroxybutyric acid) in 1,2-propylene carbonate was cooled to room temperature and diluted with an equal volume of ethanol. The precipitate was separated by filtering through a weighed filter paper, washed with ethanol and the filter with the precipitate likewise dried overnight at 110° C. and then weighed.

The filter used was an ashless, quick-run filter paper (No. 589/1) made by Schleicher and Schüll GmbH, D-3354 Dassel, West Germany.

The molecular weight determinations were carried out with an Ostwald viscometer (capillary diameter 0.3 mm) in chloroform solutions. The transit time for pure chloroform was about 65 seconds. The molecular weight was calculated using the following formula by A. Herrera de Mola et al., Makromolekulare Chemie 176, 2655–2667 (1975):

$$[\eta] = 1.9 \times 10^{-2} \, MW^{0.74}$$

where $[\eta]$ is the intrinsic viscosity and MW the molecular weight.

EXAMPLE 1

As can be seen from Table I, ethylene carbonate and 1,2-propylene carbonate differ from other solvents in that true solutions with a high PHB concentration are obtained which can be easily filtered.

Table I

Solubility of PHB in various solvents at atmospheric pressure

| Sample No. | Solvent | PHB concentration (g/liter) | Temperature (°C.) | Contact time (hrs) | PHB solubility | Properties of the "solution" |
|---|---|---|---|---|---|---|
| 1 | CHCl₃ | 200 | 50 | 10 | only just soluble | does not flow |
| 2 | CHCl₃ | 80 | 50 | 4 | — | highly viscous, filterable only with difficulty |
| 3 | dimethylsulphoxide | 15 | 120 | 10 | only just soluble | — |
| 4 | dimethylformamide | 200 | 120 | 10 | only just soluble | — |
| 5 | ethylene carbonate or propylene carbonate or dimethylformamide or dimethylsulphoxide | 3 | 100 | 2 days | only just soluble | — |
| 6 | ethylene carbonate or propylene carbonate | 200 | 120 | 3 | completely soluble | filterable |
| 7 | ethylene carbonate or propylene carbonate | 340 | 150 | 3 | — | highly viscous, filterable only with difficulty |
| 8 | ethylene carbonate or propylene carbonate | 170 | 150 | 1.2 | completely soluble | filterable |

EXAMPLE 2

Ethylene carbonate and 1,2-propylene carbonate are also significantly better than the hitherto used solvents for the extraction of PHB from fermentation masses, not only as regards the PHB yield (high concentration) and the high rate of extraction but also, as is apparent from the intrinsic viscosity, by virtue of the fact that a high molecular PHB is obtained. The extraction experiments, the results of which are summarized in Table II, were carried out as follows.

4 g of dry cells of Hydrogenomonas eutropha H-16 (Rose and Tempest, loc. cit.) containing a total of 2.8 g PHB were contacted with various solvents at various temperatures. After the times stated, an aliquot portion of each sample was filtered and PHB precipitated from the filtrate by cooling to about 40° C. The precipitate was washed with alcohol and the resulting pure PHB dried in vacuo. When chloroform, pyridine or a mixture of methylene oxide and ethanol in the volume ratio 5:1 was used as the solvent, PHB could only be precipitated by adding excess ether.

Table II

| Solvent | Temperature (°C.) | Contact time | Yield of PHB in g | Intrinsic Viscosity in chloroform [η] |
|---|---|---|---|---|
| 25 ml Ethylene carbonate | 120 | 5 min. | 0.93 | — |
| | | 15 min. | 1.52 | 2.9 |
| | | 30 min. | 1.71 | — |
| | | 3 hrs. | 2.50 | 2.3 |
| 25 ml Propylene carbonate | 120 | 5 min. | 0.85 | 4.9 |
| | | 15 min. | 0.92 | 3.9 |
| | | 30 min. | 1.82 | — |
| | | 3 hrs. | 2.61 | 4.0 |
| 25 ml chloroform | 62.5 | 2 days | 0.34⁺ | 3.5 |
| 25 ml pyridine 25 ml CH₂Cl₂: | 115 | 3 hrs. | 0.63⁺ | 1.40 |

Table II-continued

| Solvent | Temperature (°C.) | Contact time | Yield of PHB in g | Intrinsic Viscosity in chloroform [η] |
|---|---|---|---|---|
| ethanol = 5:1 | 30 | 3 hrs. | 0.21⁺ | 2.8 |

⁺ precipitation only after adding excess ether

EXAMPLE 3

In this example the rate of extraction of PHB from bacterial cells by means of 1,2-propylene carbonate was investigated. It was found that the extraction was accelerated by raising the temperature. The best yields were obtained at 120° to 140° C., the PHB decomposing to a significant extent however at higher temperatures as is apparent from the decrease in the molecular weight. The conditions which give PHB with the maximum molecular weight are a temperature range of 120° to 140° C. and a contact time of 1 to 10 minutes. If however the molecular weight is of subsidiary importance, PHB can be extracted at temperatures from over 100° C. to near the boiling point of the solvent, about 140° to 150° C. for about 25 to 30 minutes giving good results. At temperatures over 100° C. but below about 110° to 120° C. the extraction is incomplete however.

The extraction experiments, the results of which are summarized in Table III, were carried out as follows.

4 g samples of dry cells of Azotobacter chroococcum DSM 377 (Rose and Tempest, loc. cit.) each containing a total of 3 g PHB were contacted with 25 ml 1,2-propylene carbonate at the temperatures stated and filtered off. PHB was precipitated from the filtrate by cooling and adding ethanol. The precipitate was filtered off, washed with ethanol and dried overnight at 110° C.

Table III

| Time in mins. | Yield of PHB in g | | | Intrinsic Viscosity $[\eta]$ in ml $\times$ g$^{-1}$ | | | molecular weight MW $\times$ 10$^{-3}$ | | |
|---|---|---|---|---|---|---|---|---|---|
| | 110 °C. | 120 °C. | 140 °C. | 110 °C. | 120 °C. | 140 °C. | 110 °C. | 120 °C. | 140 °C. |
| 1 | — | 0.971 | 1.051 | — | 696 | 620 | — | 14.7 | 12.6 |
| 2 | 0.898 | — | — | 510 | — | — | 9.66 | — | — |
| 4 | — | 1.938 | 1.675 | — | 624 | 540 | — | 12.7 | 10.4 |
| 5 | 0.978 | — | — | 685 | — | — | 14.4 | — | — |
| 8 | — | 2.150 | 2.288 | — | 687 | 480 | — | 14.4 | 8.9 |
| 10 | 1.100 | — | — | — | — | — | — | — | — |
| 14 | — | 2.288 | 2.325 | — | 609 | 385 | — | 12.7 | 6.6 |
| 15 | 1.125 | — | — | 655 | — | — | 13.5 | — | — |
| 20 | 1.213 | 2.288 | 2.350 | — | 609 | 310 | — | 12.3 | 4.93 |
| 30 | 1.125 | — | 2.600 | 590 | 527 | 102 | 11.8 | 10.1 | 1.1 |

EXAMPLE 4

In a way similar to that of example 3, the properties of ethylene carbonate were also investigated. The results collated in Table 4 show conclusively that ethylene carbonate is a less effective extractant for PHB than 1,2-propylene carbonate and that the extracted PHB is moreover more rapidly depolymerized since none of the molecular weights determined were higher than 122,000.

The extraction experiments were carried out as follows.

4 g of dry cells of Bacillus megatherium DSM 32 (Rose and Tempest, loc. cit.) containing a total of 2.7 g PHB were contacted with 25 ml of ethylene carbonate in the way described in example 3. The PHB was isolated from the extract as in example 3.

Table IV

| Time in mins. | Yield of PHB in g 110° C. | Yield of PHB in g 140° C. | Intrinsic Viscosity. $[\eta]$ in ml $\times$ g$^{-1}$ 110° C. | Intrinsic Viscosity. $[\eta]$ in ml $\times$ g$^{-1}$ 140° C. | Molecular weight MW $\times$ 10$^{-5}$ |
| --- | --- | --- | --- | --- | --- |
| 1 | — | 1.118 | — | 65 | 0.60 |
| 2 | 0.566 | — | 120 | — | 1.37 |
| 4 | — | 1.682 | — | 40 | 0.31 |
| 5 | 0.754 | — | 110 | — | 1.22 |
| 8 | — | 2.001 | — | 25 | 0.16 |
| 10 | 0.894 | — | 65 | — | 0.60 |
| 14 | — | 1.914 | — | — | — |
| 20 | 0.954 | 1.856 | 55 | — | 0.48 |
| 30 | 0.983 | 1.551 | 47 | — | 0.39 |

EXAMPLE 5

This example shows that PHB can be extracted rapidly and very well from previously untreated cells with ethylene carbonate or 1,2-propylene carbonate. Although there is hardly any difference in yield, there are differencies as regards the molecular weight of the isolated PHB.

The extraction experiments, the results of which are summarized in Table V, were carried out as follows.

A fermentation solution of Hydrogenomonas eutropha H-16 was centrifuged to give 12 g cell sediment containing 2.75 g PHB in 4.3 g total solids. The wet fermentation mass was suspended in 25 ml of solvent and heated with stirring to 120° C. Samples were withdrawn at intervals, filtered at 120° C. and the PHB isolated from the filtrate as in example 3.

Table V

| Time in minutes | Yield of PHB in g ethylene carbonate | Yield of PHB in g 1,2-propylene carbonate | Intrinsic Viscosity $[\eta]$ in ml $\times$ g$^{-1}$ | Molecular Weight MW $\times$ 10$^{-5}$ |
| --- | --- | --- | --- | --- |
| 18 | — | 1.232 | 507 | 9.58 |
| 25 | 1.559 | — | 109 | 1.20 |
| 31 | — | 1.610 | 473 | 8.72 |
| 39 | — | 1.836 | — | — |
| 41 | 1.938 | — | — | — |
| 44 | — | 2.108 | 350 | 5.81 |
| 48 | 2.176 | — | — | — |
| 60 | 1.904 | — | — | — |

EXAMPLE 6

Extraction of PHB from native cell masses with ethylene carbonate

This example is intended to show how PHB may be isolated in high yield from native cells using ethylene carbonate without prejudicing the direct reuse of the ethylene carbonate.

12 g of fermentation mass sediment containing 2.9 g PHB were taken up in 25 ml ethylene carbonate and heated with stirring to about 118° to 130° C. After a 44 minute extraction time the hot suspension was suction filtered to remove the cells. An aliquot portion A of the filtrate was then cooled to about 40° C. and the precipitated PHB filtered off, washed with alcohol and dried in vacuo. 1.56 g of PHB were obtained. 5 to 10% by vol. of water were added to an aliquot part B of the filtrate. PHB was precipitated immediately and 2.1 g of PHB, which was identical with an authentic sample, was isolated by filtering at 90° to 100° C. in the usual way. The resulting filtrate was used three more times to extract PHB from native cell masses with virtually the same result.

EXAMPLE 7

Extraction of PHB from native cell masses with 1,2-propylene carbonate

This example is intended to show how pure PHB may be obtained practically quantitatively from native cells using 1,2-propylene carbonate without prejudicing the direct reuse of the 1,2-propylene carbonate.

11.5 g of fermentation mass were taken up in 25 ml 1,2-propylene carbonate and heated with continuous stirring to 119° to 135° C. and held for about 40 to 50 minutes at 119° to 135° C. After suction filtering the hot suspension, 1 to 5 ml of water were added with stirring to the filtrate. PHB precipitated immediately. The resulting suspension was filtered at room temperature and the filter cake washed well with ethanol and dried in vacuo. 95% of the PHB in the cell mass was extracted. The melting point of the product obtained lay between 174° and 178° C. and was unaltered by two recristallisations from chloroform/ether. Analysis of the product gave the following values: calculated for $(C_4H_6O_2)_n$: C 55.8%, H 6.96%, N 0.0%, ash 0.0%. found: C 55.7%, H 6.28%, N 0.0%, ash 0.0%.

The 1,2-propylene carbonate obtained as the last filtrate was subsequently used three more times without any kind of preparation to isolate pure PHB from native cells with the same success.

EXAMPLE 8

Pure PHB was successfully extracted in the way described in example 7 from native fermentation masses of all of the microorganisms listed by Rose and Tempest (loc. cit.) and Schlegel and Gottschalk (loc. cit.).

EXAMPLE 9

Extraction of PHB from wet cells with 1,2-propylene carbonate

This example is intended to show how PHB can be isolated from wet cells with 1,2-propylene carbonate and how the yield depends on the contact time.

For this experiment 11.25 g of wet cells from an autotropic fermentation with Hydrogenomonas eutropha H-16 were used. The dry weight of the cells was 39% of the wet weight, i.e. they contained 4.39 g dry cell material. The dry cell material contained about 40% or 1.76 g PHB. The wet cells were mixed with 150 ml 1,2-propylene carbonate which had been heated to 120° C. The temperature was held constant and the suspension stirred. 10 ml samples were removed by pipette at the intervals given in Table VI. Sampling took a maximum of 10 seconds. The samples were filtered hot. On cooling to room temperature PHB precipitated. To the cooled samples was added an equal volume of acetone, the PHB separated by filtering through weighed ashless, quick-run filter papers and dried at 110° C.

Table VI

| Time (minutes) | PHB (mg) | Yield (%) | Intrinsic Viscosity $[\eta]$ in ml $\times$ g$^{-1}$ | Molecular Weight MW $\times$ 10$^{-5}$ |
|---|---|---|---|---|
| 1.5 | 53.6 | 45.7 | 566 | 11.1 |
| 4 | 78.3 | 66.7 | — | — |
| 7.5 | 85.20 | 72.6 | 333 | 5.4 |
| 10.5 | 94.2 | 80.3 | 279 | 4.27 |
| 15 | 91.6 | 78.0 | — | — |
| 20 | 102.9 | 87.7 | 251 | 3.7 |
| 25 | 103.4 | 88.0 | — | — |
| 30 | 103.8 | 88.5 | 267 | 4.03 |
| 40 | 108.4 | 92.4 | 63 | 0.57 |
| 52 | 113.0 | 96.3 | — | — |

As the Table shows, high yields are obtained in a short time. These yields can also be achieved without adding acetone. The rate of extraction appears to be independent of the water content.

EXAMPLE 10

This example describes the continuous extraction of PHB with 1,2-propylene carbonate.

For this experiment an ideal flow tube reactor was used which was held at 110° C. with a thermostat. The reactor was provided with a stirrer and had a volume of 180 ml and a Bodenstein number between 26 and 40. The wet cells were dried with acetone. 128 g of dry cell mass containing about 20% PHB were used per liter of 1,2-propylene carbonate. The dry cell mass was mixed continuously at room temperature with the 1,2-propylene carbonate in a vessel provided with a stirrer and then passed through the reactor held at 110° C. After leaving the reactor, the cell mass was filtered off hot in a heated quick-filtration apparatus, e.g. a centrifuge. PHB precipitated from the PHB extract on cooling. The dependence of the PHB yield on the dwell time ($\tau$) in the reactor can be seen from Table VII.

Table VII

| $\tau$ (minutes) | 1.6 | 1.85 | 2.45 | 2.9 |
|---|---|---|---|---|
| Yield (%) | 55 | 56 | 70 | 78 |

The continuous extraction can be carried out on an Industrial scale by mixing the moist cell mass in a heated mixing vessel with the 1,2-propylene carbonate so that the water evaporates from the cell mass in the mixing vessel. Short dwell times in the reactor give high molecular PHB, long dwell times and high temperatures low molecular PHB.

EXAMPLE 11

Ethylene carbonate and 1,2-propylene carbonate are particularly suitable as solvents for poly-($\beta$-hydroxybutyric acid) produced synthetically from racemic $\beta$-hydroxybutyric acid.

150 g of chemically synthesized optically inactive poly-($\beta$-hydroxybutyric acid) were dissolved at 140° C. in 1 liter of ethylene carbonate or 1,2-propylene carbonate. The solutions could be filtered without losses and the poly-($\beta$-hydroxybutyric acid) precipitated in the same way as in example 7.

EXAMPLE 12

Both ethylene carbonate and 1,2-propylene carbonate are suitable as solvents for use in the wet spinning of racemic and optically active poly-($\beta$-hydroxybutyric acid). About 10% to 20% solutions of poly-($\beta$-hydroxybutyric acid) in ethylene carbonate and 1,2-propylene carbonate respectively were spun through a nozzle into a precipitating bath consisting of about 50% by vol. water and about 50% by vol. ethylene carbonate or 1,2-propylene carbonate respectively. The delivery speed of the filament was about 8 m per minute.

What is claimed is:

1. A process which comprises:
    extracting poly-($\beta$-hydroxybutyric acid) from a moist or dry cell mass of a microorganism which forms poly-($\beta$-hydroxybutyric acid) by suspending the cell mass in a liquid cyclic carbonic acid ester of the formula:

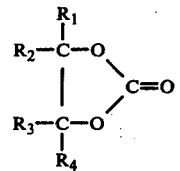

wherein $R_1$, $R_2$, $R_3$ and $R_4$, which are the same or different, are hydrogen or alkyl with 1 to 6 carbon atoms, as a solvent for the poly-($\beta$-hydroxybutyric acid),
    heating the suspension with stirring to a temperature above 100° C.,
    separating the cell mass from the hot solvent extract,
    cooling the hot solvent extract to precipitate poly-($\beta$-hydroxybutyric acid), and
    wet spinning the precipitated poly-($\beta$-hydroxybutyric acid).

2. A process according to claim 1 in which the poly-($\beta$-hydroxybutyric acid) is the dextro optical isomer.

3. A process which comprises:
    preparing a solution of poly-($\beta$-hydroxybutyric acid) in a cyclic carbonic acid ester solvent, or mixture thereof, of the formula

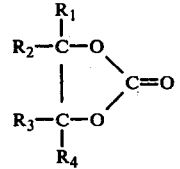

wherein $R_1$, $R_2$, $R_3$ and $R_4$, which may be the same or different, are hydrogen or alkyl with 1 to 6 carbon atoms, and
    wet spinning the solution through a nozzle into an aqueous bath mixture containing at least one of the solvents of the above formula.

4. A process according to claim 3 in which the solvent is ethylene carbonate, 1,2-propylene carbonate or a mixture thereof.

5. A process for wet spinning chemically synthesized racemic or optically active poly-(β-hydroxybutyric acid) which comprises:

dissolving said poly-(β-hydroxybutyric acid) in a liquid cyclic carbonic acid ester of the formula:

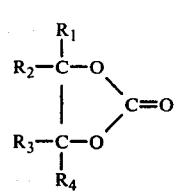

wherein $R_1$, $R_2$, $R_3$ and $R_4$, which are the same or different, are hydrogen or alkyl with 1 to 6 carbon atoms, and spinning the solution thus obtained through a nozzle into a precipitating bath consisting of about 50% by vol. water and about 50% by vol. of said liquid cyclic carbonic acid ester.

6. A process according to claim 5 in which the solvent is ethylene carbonate, 1,2-propylene carbonate or a mixture thereof.